(12) United States Patent
Omura et al.

(10) Patent No.: US 6,689,066 B1
(45) Date of Patent: Feb. 10, 2004

(54) ULTRASONIC PROBE

(75) Inventors: Masayoshi Omura, Saitama (JP); Hiroshi Fukuda, Hachioji (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/309,390

(22) Filed: Dec. 3, 2002

(51) Int. Cl.$^7$ ................................. A61B 8/12
(52) U.S. Cl. ...................................... 600/463
(58) Field of Search .................. 600/459–471, 600/486–488, 505, 585; 601/2–4; 604/93.01–172

(56) References Cited

U.S. PATENT DOCUMENTS

| | | | |
|---|---|---|---|
| 4,994,047 A | * | 2/1991 | Walker et al. ............... 604/264 |
| 5,226,899 A | * | 7/1993 | Lee et al. .................... 604/282 |
| 5,300,032 A | * | 4/1994 | Hibbs et al. ................. 604/164 |
| 5,342,386 A | * | 8/1994 | Trotta ......................... 606/194 |
| 5,803,083 A | * | 9/1998 | Buck et al. .................. 600/439 |
| 5,865,801 A | * | 2/1999 | Houser ......................... 604/96 |
| 6,185,449 B1 | * | 2/2001 | Berg et al. ................... 600/435 |

* cited by examiner

Primary Examiner—Francis J. Jaworski
(74) Attorney, Agent, or Firm—Ostrolenk, Faber, Gerb & Soffen, LLP (57) ABSTRACT

An ultrasonic transducer is provided at the distal end of a sheath included in an inserting portion of an ultrasonic probe for performing ultrasonic diagnosis. The ultrasonic transducer can transmit and receive ultrasound through an acoustic window 38 facing against the ultrasonic transducer through an acoustic medium filled around the ultrasonic transducer. At least the acoustic window is formed of a resin including a mixture of polyamide block and polyether ester block copolymer resin and polyurethane. Thus, multiple reflection, for example, can be reduced in the vicinity of the acoustic windows. Furthermore, the sheath portion may be formed of the same resin. Thus, the sheath portion can be inserted through an endoscope channel, for example, smoothly with less buckling.

20 Claims, 5 Drawing Sheets

ULTRASONIC PROBE

This application claims benefit of Japanese Application No. 2000-164835 filed on Jun. 1, 2000, the contents of which are incorporated by this reference.

BACKGROUND OF THE INVENTION

Field of the Invention and Description of the Related Art

The present invention relates to an ultrasonic probe including ultrasonic transducer to be used for ultrasonic observation.

Conventionally, resin such as polyethylene and polytetrafluoroethylene is used as a sheath material of a mechanical scanning type ultrasonic miniature probe. However, in an acoustic window portion of the sheath, which touches an object and allows ultrasound to pass through, the object and the sheath material have different acoustic impedances. Therefore, for example, the sensitivity (transmission coefficient) of ultrasound is reduced due to reflection of ultrasound occurred at the interface. Images are deteriorated due to multiple reflection at an interface. As a material for improving the acoustic matching, polyamide block and polyether ester block copolymer resin is disclosed in Japanese Examined Patent Application Publication No. 6-57211.

However, the flexibility of the polyamide block and polyether ester block copolymer resin disclosed in the Japanese Examined Patent Application Publication No. 6-57211 tends to decrease as the chemical resistance and the heat resistance increase. Therefore, when an ultrasonic miniature probe having a sheath of polyamide block and polyether ester block copolymer resin sheath with higher chemical resistance is inserted through an endoscope channel, the miniature probe may easily buckle due to steep bending of the endoscope.

OBJECTS AND SUMMARY OF THE INVENTION

It is an object of the present invention to provide an ultrasonic probe, which hardly buckles even when the ultrasonic probe is inserted through an endoscope channel or the like and which can reduce multiple reflection in the vicinity of an acoustic window.

It is another object of the present invention to provide an ultrasonic probe, which can reduce multiple reflection at least in the vicinity of an acoustic window.

There is provided an ultrasonic probe, including:

a long and narrow flexible sheath;

a cover member covering a hollow portion provided on a distal end side of the sheath in a liquid-tight manner;

an ultrasonic transducer, which is placed within the hollow portion covered by the cover member, for transmitting and receiving ultrasound;

an acoustic medium, which is filled around the ultrasonic transducer, for conducting ultrasound; and an acoustic window portion, which faces against an transmitting and receiving surface for transmitting and receiving ultrasound of the ultrasonic transducer in the cover member and which is formed of a resin including a mixture of polyamide block and polyether ester block copolymers and polyurethane, for allowing ultrasound to pass through. Thus, the difference from the acoustic impedance of a living body can be reduced relatively. Therefore, the multiple reflection can be reduced. Furthermore, the sheath may also be formed of the resin. Thus, the sheath can be inserted into an endoscope channel without buckling.

BRIEF DESCRIPTION OF THE DRAWINGS

FIGS. 1 to 3 relate to a first embodiment of the present invention.

DESCRIPTION OF THE PREFERRED EMBODIMENTS

Embodiments will be described below with reference to drawings.

First Embodiment

A first embodiment of the present invention will be described concretely with reference to FIGS. 1 to 3.

Figure 1:
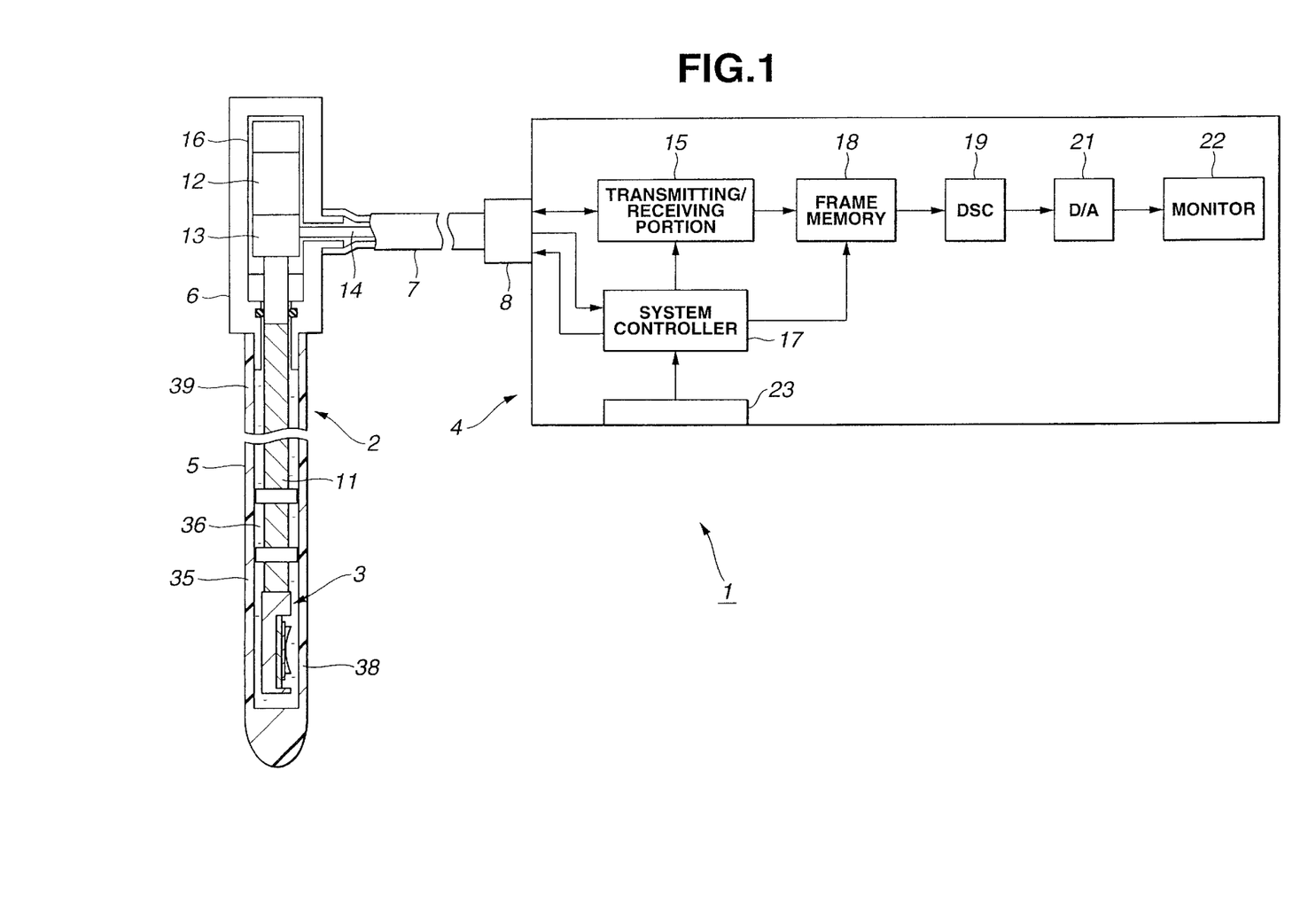
FIG. 1 is a block diagram showing an entire construction of an ultrasonic diagnostic system including the first embodiment of the present invention.

As shown in FIG. 1, an ultrasonic diagnostic system 1 includes an ultrasonic probe 2, which is inserted into a body cavity, for example, for exchanging ultrasound with an object. The ultrasonic diagnostic system 1 further includes an ultrasonic diagnostic equipment 4 connected to the ultrasonic probe 2 for performing signal processing for an ultrasonic transducer 3 incorporated in the ultrasonic probe 2 and for displaying an ultrasonic image.

The ultrasonic probe 2 includes a flexible, long and narrow inserting portion 5 a grasping portion 6 a cable portion 7 and a connector 8 The inserting portion 5 is inserted through a body cavity or a channel 56 (see FIG. 3) of an endoscope 41. The grasping portion 6 is provided at the rear end of the inserting portion 5 The cable portion 7 is extended from the grasping portion 6. The connector 8 is provided at the end of the cable portion 7 The connector 8 is connected to the ultrasonic diagnostic equipment 4 removably.

A flexible shaft 11, for example, is provided within the inserting portion 5 of the ultrasonic probe 2. The ultrasonic transducer 3 is mounted on the distal end side of the flexible shaft 11. The rear end of the flexible shaft 11 is connected to a motor 12 provided within the grasping portion 6, for example. When the motor 12 rotates, the flexible shaft 11 and the ultrasonic transducer 3 are rotationally driven. Thus, radial scanning can be performed mechanically.

The ultrasonic transducer 3 is connected to a coaxial cable, not shown. The coaxial cable is connected to a slip ring 13 within the grasping portion 6 through a hollow portion of the flexible shaft 11. A cable 14 connected to a stator side constant of the slip ring 13 is connected to a transmitting/receiving portion 15 for transmitting and receiving within the ultrasonic diagnostic equipment 4.

The motor 12 and a rotary encoder 16 for detecting a rotation angle of the motor 12 are connected to a system controller 17 within the ultrasonic diagnostic equipment 4 through the cable 14.

The system controller controls rotation and transmitting and receiving by the motor 12. The transmitting/receiving portion 15 applies a transmitted pulse to the ultrasonic transducer 3 to transmit ultrasound. In addition, the ultrasonic transducer 3 receives ultrasound reflected by the object. The echo signals are converted to electric signals, which are then converted to digital signals by an A/D converter, not shown. Then, the digital signals are written in a frame memory 18 temporarily under control of the system controller 17.

The echo signal data written in the frame memory 18 is radial sound ray data. The echo signal data is converted to orthogonal coordinate system data by a digital scan converter (abbreviated as DSC) 19 and then is output to a monitor 22 through a D/A converter 21. Thus, an ultrasonic image is displayed.

A switch for variably setting characteristics of STC is provided at a front panel 23 of the ultrasonic diagnostic equipment 4.

Figure 2:
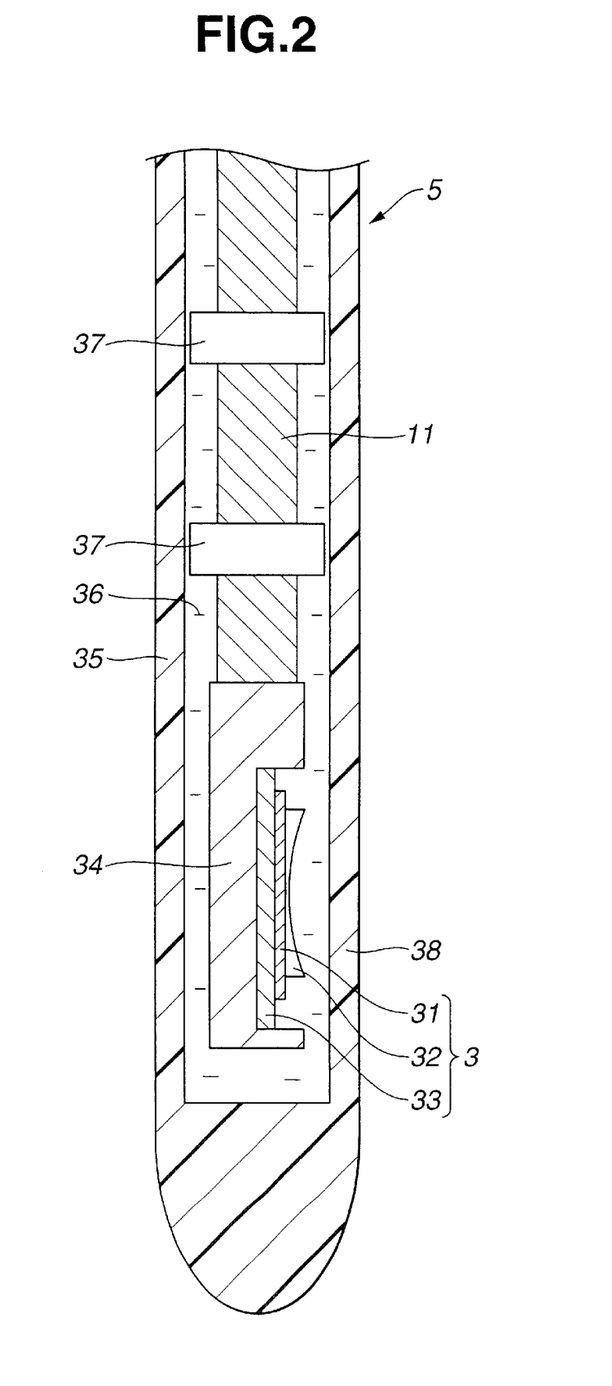
FIG. 2 is a section diagram showing a construction of a distal end side of an ultrasonic probe according to the first embodiment of the present invention.

FIG. 2 shows a construction of the ultrasonic transducer 3 placed on the distal end side of the ultrasonic probe 2.

The ultrasonic transducer 3 comprises a plate-like piezoelectric transducer 31, a focusing acoustic lens 32 of epoxy resin, for example, and a backing layer 33 of ferrite rubber, for example. The piezoelectric transducer 31 has a piezoelectric characteristic for electric-acoustic conversion. The acoustic lens 32 is provided on a transmitting/receiving surface (front surface, here) for transmitting and receiving ultrasound in the piezoelectric transducer 31. The backing layer 33 is provided on a back surface of the piezoelectric transducer 31 for attenuating ultrasound.

In the ultrasonic transducer 3, the backing layer 33 is bonded and is fixed to a housing 34. The housing 34 is mounted at the distal end of the flexible shaft 11. Electrodes, not shown, are provided on both surfaces of the piezoelectric transducer 31. The signal electrode on the transmitting and receiving surface side having the acoustic lens 32 is electrically connected to a ground line of the coaxial cable, not shown, through the hollow portion of the flexible shaft 11. The electrode on the backing layer 33 side is electrically connected to a signal line of the coaxial cable. The coaxial cable is removably connected to the ultrasonic diagnostic equipment 4 through the connector 8.

The ultrasonic transducer 3 and the flexible shaft 11 are provided within a flexible sheath distal end portion 35 and sheath body portion (sheath rear end portion) 39, which are included in a skin of the inserting portion 5.

An acoustic medium 36 such as water and liquid paraffin for conducting ultrasound is filled between the ultrasonic transducer 3 and the sheaths (35 and 39).

In other words, according to this embodiment, the hollow sheaths forming the skin of the flexible inserting portion 5 includes the hollow, long and narrow sheath body portion 39 and the sheath distal end portion 35 integrally formed at the distal end of the sheath body portion 39. The distal end of the sheath distal end portion 35 is closed in a substantially semicircular form. The ultrasonic transducer 3 is accommodated within the hollow portion in the sheath distal end portion 35.

A bearing 37 is provided on the distal end side of the flexible shaft 11. Thus, the ultrasonic transducer 3 can be rotationally driven for performing radial scanning without rattling.

A part facing against the ultrasonic transducer 3 in the sheath distal end potion 35 is provided with a through-ultrasound window portion (acoustic window) 38, which allows ultrasound to pass through.

An O-ring for keeping liquid-tightness is provided between the base end of the sheath body portion 39 and the substantially front end of the grasping portion 6 which are connected in the liquid-tight manner.

In this embodiment, the material of the sheaths (35 and 39) may be resin containing a mixture of polyether block amide (one of polyamide block and polyether ester block copolymers) and polyurethane. Thus, the flexible sheath can be obtained having an acoustic impedance close to that of a living body ($1.5 \times 10^6$ [kg/($m^2$S)]) and chemical resistance, which is not damaged. Therefore, when the sheath is inserted through an endoscope channel, the sheath hardly buckles.

The table below shows acoustic characteristics of the sheath material according to this embodiment and a conventional sheath material.

TABLE

| SHEATH MATERIALS | DENSITY p kg/$m^3$ | SOUND VELOCITY c m/s | ACOUSTIC IMPEDANCE p × $10^6$ [kg/ ($m^2 \cdot$ s)] |
| --- | --- | --- | --- |
| RESIN CONTAINING MIXTURE OF POLYETHER BLOCK AND POLYURETHANE | 1028 | 1905 | 1.96 |
| POLYETHYLENE (CONVENTIONAL) | 937 | 2190 | 2.05 |

Next, operations of this embodiment will be described.

Figure 3:
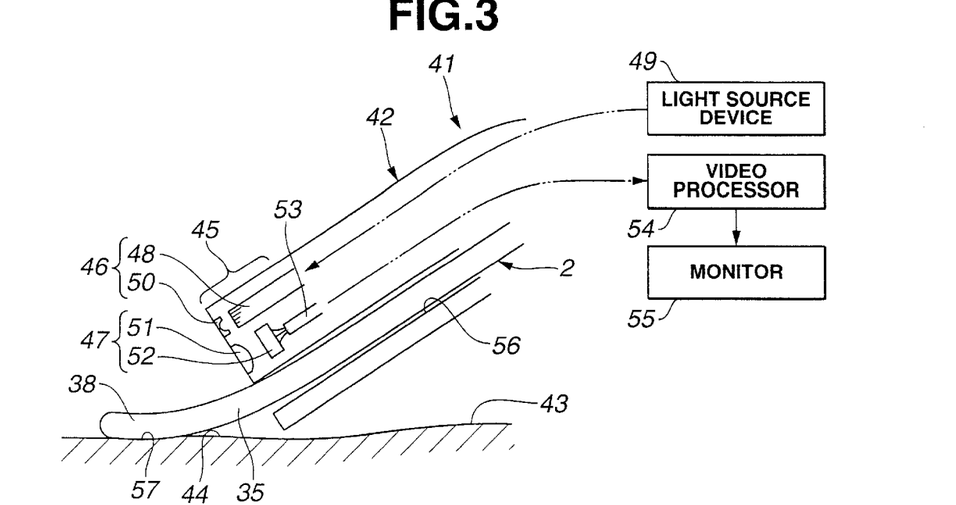
FIG. 3 is a diagram showing a state where an ultrasonic probe is inserted through a channel of an endoscope to ultrasonically diagnose a part of interest.

First of all, as shown in FIG. 3, an inserting portion 42 of an endoscope 41 is inserted through a tube cavity 43. A part 44 to be examined such as an internal wall of the tube cavity 43 can be observed optically by using an optical illumination unit 46 and an observing (imaging) unit 47 at a distal end portion 45 of the inserting portion 42.

In other words, a light guide 48 for conducting illuminating light is provided in the inserting portion 42. The light guide 48 conducts the illuminating light generated by a light source device 49. The conducted illuminating light is emitted from the distal end surface fixed at an illuminating windows of the distal end portion 45 to the part 44 to be examined side through an illuminating lens 50.

An optical image of the part 44 illuminated by the illuminating light emitted from the illuminating optical system 46 is formed at a charge-coupled device (abbreviated as CCD) 52 by an objective optical system 51. The optical image is optoelectronically transduced. The objective optical system 51 included in the imaging unit 47 is mounted at the observation window. The CCD 52 is a solid-state image sensing device provided at an image-forming position.

The CCD 52 is connected to a video processor 54 through a cable 53 lying within the inserting portion 42. The video processor 54 performs signal processing. An image imaged by the CCD 52 undergoes the signal processing and is converted to video signals. Then, the image is displayed on a display surface of a monitor 55 as an endoscopic image.

An operator can perform optical examination by using the endoscope 41 with reference to the endoscope image displayed on the monitor 55. When an acoustic examination is required in addition to the optical examination, the ultrasonic probe 2 is inserted through a surgical instrument channel 56 of the endoscope 41 from the insertion hole. As shown in FIG. 1, the connector 8 of the ultrasonic probe 2 is connected to the ultrasonic diagnostic equipment 4.

In this case, the sheaths (35 and 39) included in the inserting portion 5 of the ultrasonic probe 2 are flexible and are hard moderately. Therefore, even when the inserting portion 42 of the endoscope 41 within the tube cavity 43 is bent steeply, the inserting portion 42 does not buckle and can be inserted smoothly and fast. The distal end side of the sheath may be projected from the distal end opening of the channel 56. Thus, the acoustic window 38 can come in contact with a part 57 of interest to be examined in detail.

By turning ON a switch, not shown, for transmitting and receiving ultrasound, the motor 12 rotates and the ultrasonic transducer 3 is rotationally driven through the flexible shaft 11.

The rotation is detected by the rotary encoder 16. In synchronous with the rotation, a transmitted pulse is applied from the transmitting/receiving portion 15 to the piezoelectric transducer 31 of the ultrasonic transducer 3. Ultrasound is excited by the piezoelectric transducer 31 and is converged at the acoustic lens 32. Thus, the ultrasound is sent in a pulse manner.

The ultrasound propagates through the acoustic medium 36 and passes through the acoustic window 38 in the sheath facing against the ultrasonic transducer 3. Then, the ultrasound is emitted to the living body side in contact with the acoustic window 38.

In this case, the acoustic impedance of the living body is substantially $1.5 \times 10^6$ [kg/(m$^2$s)]. The acoustic impedance of the sheath 35 of the acoustic window 38 is close to the value of the living body. Therefore, the reflection wave of ultrasound can be smaller than that of the conventional art on the contact surface of the external surface of the sheath distal end portion 35 and the living body.

The ultrasound emitted to the living body side is reflected by a part having different acoustic impedance.

The reflected ultrasound reverses and is received by the piezoelectric transducer 31. Then, the ultrasound is converted to electric signals, that is, echo signals. The echo signals are detected and are amplified by the transmitting/receiving portion 15 and then are A/D converted. Sound ray data (ultrasonic data) is sequentially stored in the frame memory 18.

The sound ray data is converted to sound ray data in an orthogonal coordinate system by the DSC 19. The sound ray data is converted to analog video signals by the D/A converter 21. The analog video signals are output to the monitor 22 along with a synchronous signal, not shown. Then, an ultrasonic image is displayed on a display surface of the monitor 22.

According to this embodiment, the entire sheath, which is included in the skin of the inserting portion 5 of the ultrasonic probe 2, including the acoustic window portion 38, is formed of a resin including a mixture of polyamide block and polyether ester block copolymers and polyurethane. Therefore, the sheath is flexible and can be inserted through the channel 56 of the endoscope 41 smoothly without buckling for performing ultrasonic examination. In addition, the value of the acoustic impedance of the acoustic window portion 38 is close to that of a living body. Therefore, the image quality deterioration due to reflection can be reduced.

Because of the good chemical resistance, the sheath can be easily disinfected by a disinfectant, for example, for ultrasonically diagnosing a living body. Thus, the inserting portion 5 can be used for a long period of time repeatedly.

The entire sheath is formed of a single resin. Therefore, an ultrasonic probe can be produced at low costs.

Second Embodiment

Figure 4:
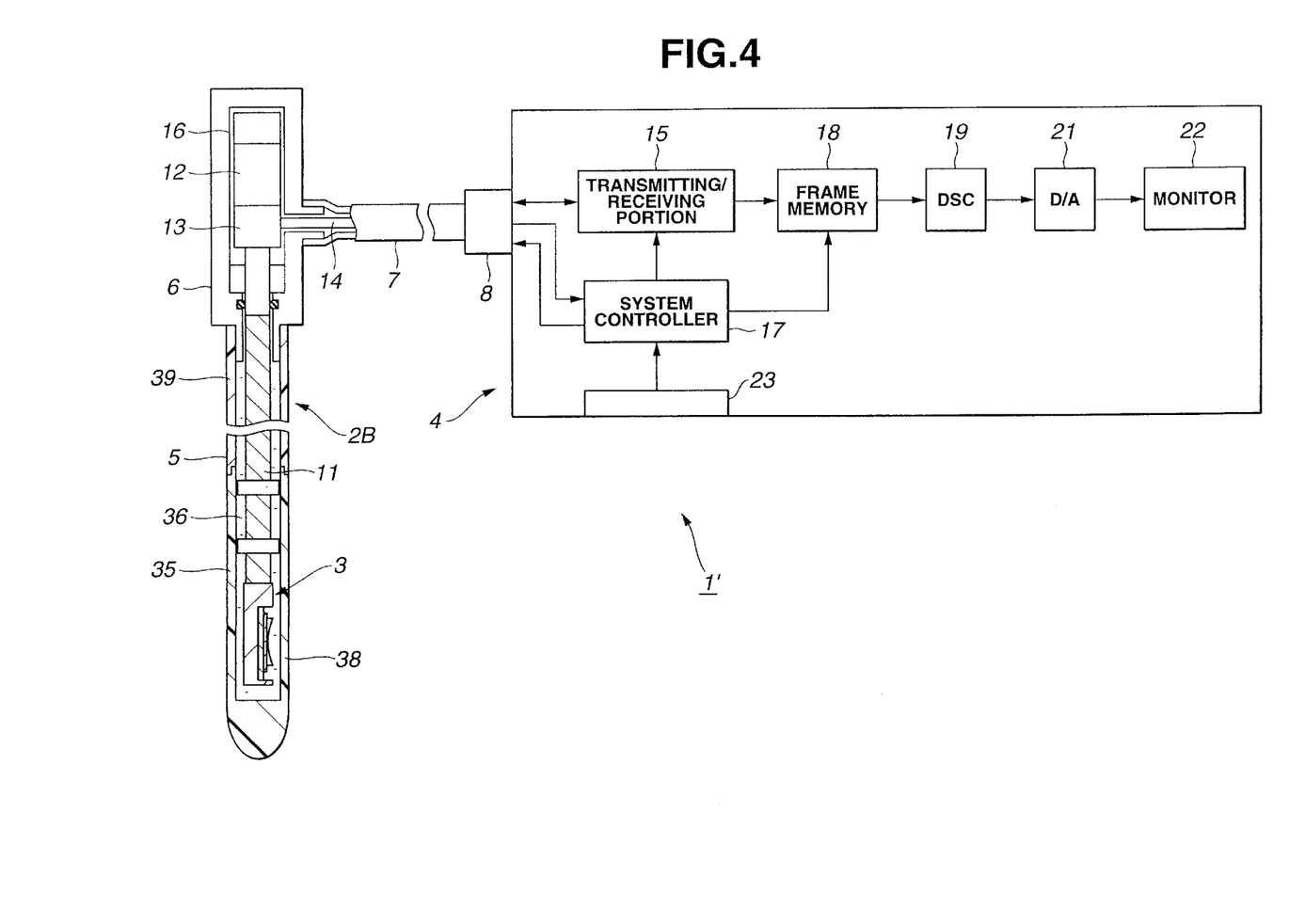
FIG. 4 is a block diagram showing an entire construction of an ultrasonic diagnostic system including a second embodiment of the present invention.

A second embodiment of the present invention will be described next with reference to FIG. 4. FIG. 4 is an ultrasonic diagnostic system 1' including an ultrasonic probe 2B according to the second embodiment.

An inserting portion 5 of the ultrasonic probe 2B according to this embodiment has a sheath body portion 39 and a sheath distal end portion 35. The sheath body portion 39 is included in a skin of the inserting portion 5. The sheath distal end portion 35 is connected to the distal end of the sheath body portion 39 in a liquid-tight manner. The sheath body portion 39 and the sheath distal end portion 35 include materials containing substances in different mixing rates.

According to this embodiment, the sheath distal end portion 35 functions as a cover for covering, in a liquid-tight manner, a hollow accommodating an ultrasonic transducer 3. Thus, the sheath distal end portion 35 is formed of a resin containing a mixture of polyamide block and polyether ester block copolymers and polyurethane, for example. The part facing against the ultrasonic transducer 3, including the acoustic window 38, can have an acoustic impedance value closer to the acoustic impedance value of a living body.

On the other hand, the sheath body portion 39 of the sheath, which is included in the main part of the long inserting portion 5 is formed of a resin including a mixture of the polyamide block and polyether ester block copolymers and polyurethane in a different mixture rate. Thus, the sheath body portion 39 can be more flexible than the sheath distal end portion 35. In other words, the sheath distal end portion 35 and the sheath body portion 39 is formed of resins including mixtures in different mixing rates, respectively. The sheath distal end portion 35 is connected to the distal end of the sheath body portion 39 in a watertight manner.

According to this embodiment, the shorter distal end portion of he inserting portion 5 has an acoustic impedance closer to that of a living body. Therefore, the multiple reflection and so on can be suppressed on the interface. In addition, the inserting portion 5 is flexible and constitutes sheaths, which hardly buckle. Thus, the inserting portion 5 can be inserted through an endoscope channel without buckling.

When a part in the vicinity of the acoustic window 38 on the distal end side is deteriorated due to rotational driving for a long period of time, only the sheath distal end portion 35 may be replaced. Thus, the repair or maintenance can be performed at low costs. The rear end portion of the sheath 35 and the sheath distal end portion 35 may be connected through a ring-shaped connecting member, for example, such that they can be replaced easily.

Third Embodiment

Figure 5:
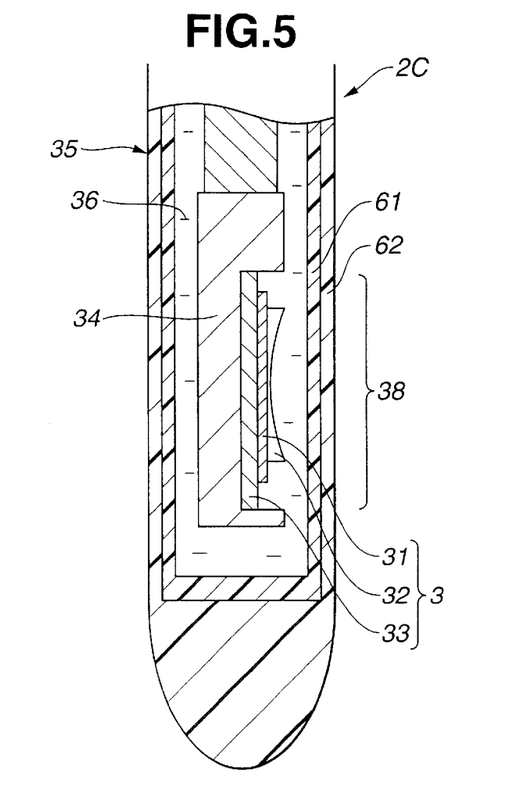
FIG. 5 is a section diagram showing a construction of a distal end side of an ultrasonic probe according to a third embodiment of the present invention.

A third embodiment according to the present invention will be described next with reference to FIG. 5. FIG. 5 shows a construction of a part in the vicinity of an acoustic window 38 on the distal end side of an ultrasonic probe 2C according to the third embodiment.

This embodiment is different from the first and second embodiments in that the sheath part providing with at least the acoustic window 38 of the sheath distal end portion 35 forms a laminate structure having a first resin layer 61 and second resin layer 62 containing mixtures of the polyamide block and polyether ester block copolymers and polyurethane in different mixing rates.

In other words, the acoustic window 38 constitutes two resin layers in different mixing rates. In this case, the internal first resin layer 61 has an acoustic impedance set to be closer to the acoustic impedance of the acoustic medium 36. The external second resin layer 62 has an acoustic impedance set to be closer to the acoustic impedance of a living body.

In this way, the acoustic window 38 may constitute two resin layers having an acoustic impedance, which is middle of the acoustic impedances of the acoustic medium 36 and a living body. In this case, a difference between both of the acoustic impedances can be reduced more than the acoustic window having one layer. In other words, by increasing a number of levels of acoustic impedance, each of the impedances can be reduced. As a result, the reflection of ultrasound can be reduced at the boundary of the acoustic window 38 and a living body side and at the boundary of the acoustic medium 36 and the acoustic window 38.

The rest have the same effects as those of the first and second embodiments.

The case where the ultrasonic transducer 3 is rotationally driven has been described above. However, a case where the ultrasonic transducer 3 is driven so as to swing is applicable. A case where the ultrasonic transducer 3 rotationally driven in a spiral form is also applicable.

The embodiments have valid effects for a case where the ultrasonic transducer 3 is driven mechanically. However, the present invention can be applied to electronical scanning.

In the above-described embodiments, the ultrasonic transducer 3 is provided at the distal end of the ultrasonic probe 2. However, the present invention is apparently not limited thereto. The present invention can be applied to an ultrasonic endoscope having endoscopic functions, that is, optical observation units (an optical illuminating unit, an optical observation unit and/or an imaging unit) in addition to an ultrasonic transducer on the distal end side of the probe.

Figure 6:
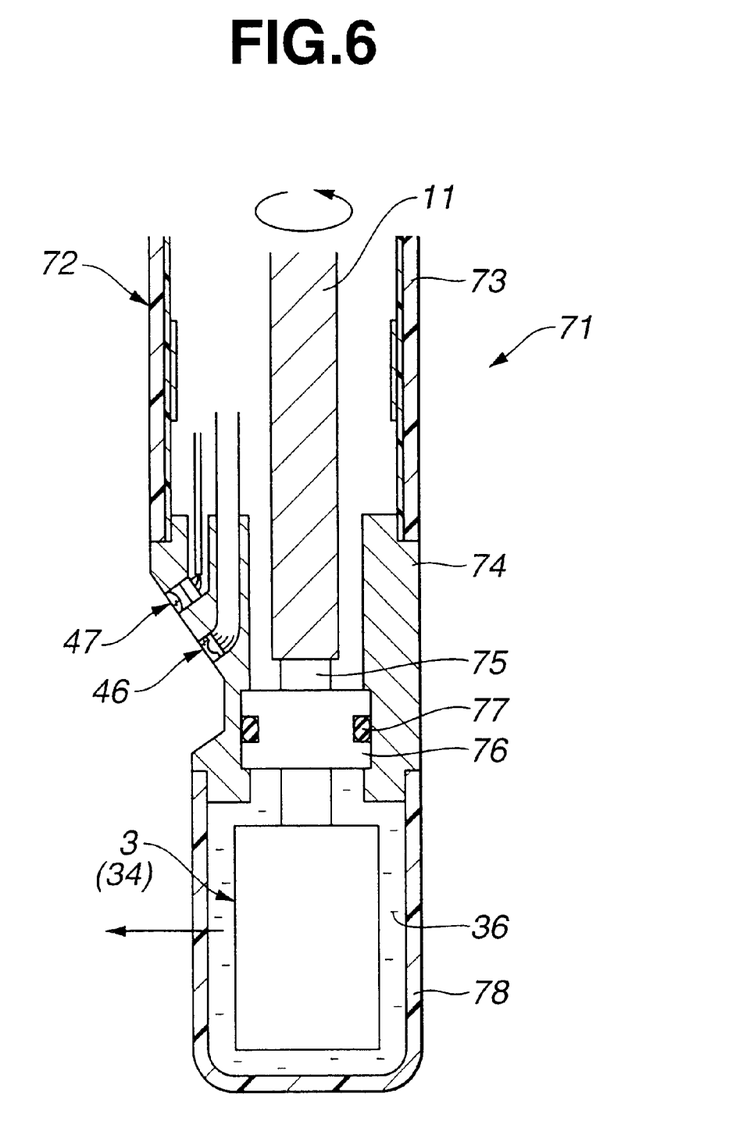
FIG. 6 is a diagram showing a construction of a distal end side of an ultrasonic endoscope including an endoscopic function at the ultrasonic probe.

FIG. 6 shows an ultrasonic endoscope 71 having endoscopic functions, which is a variation example of an ultrasonic probe.

A hard distal end member 74 is mounted in a watertight (liquid-tight) manner at the distal end of a flexible and hollow sheath 73 made up in a soft inserting portion 72. An illuminating unit 46 and an imaging unit 47, which are basically the same as those in FIG. 3, are provided on a slanting surface of the distal end member 74.

The distal end member 74 has a hollow in a longitudinal direction of the sheath 73. A hard shaft 75 mounted at the distal end of the flexible shaft 11 is rotatably held by the distal end member 74 at a bearing portion 76.

A housing 34 having the ultrasonic transducer 3 is mounted at the distal end of the hard shaft 75.

A distal end cap 78 filled with the acoustic medium 36 covers in a liquid-tight manner around the ultrasonic transducer 3.

The distal end cap 78 is formed of the resin having a mixture of polyamide block and polyether ester block copolymers and polyurethane. Especially, the part facing against the ultrasonic transducer 3 has the acoustic window 38, which allows ultrasound to pass through.

The bearing portion 76 has a ring-shaped depression. An O-ring 77 for water-tightness is provided thereto. Thus, the O-ring 77 can prevent the acoustic medium 36 from leaking toward the rear side.

In other word, in this embodiment, the distal end cap (cover member) 78 covering the hollow portion accommodating the ultrasonic transducer 3 is provided in a liquid-tight manner at the distal end of the sheath 73 constituted in the inserting portion 72 through the hard distal end member 74.

Endoscopic observation can be implemented by using the optical illuminating optical system 46 and the imaging unit 47 provided at the distal end member 74 of the ultrasonic endoscope 71 according to this embodiment. In this case, in order to implement acoustic observation, the distal end cap 76 is abutted with an object. Thus, ultrasonic diagnosis can be performed.

The inserting portion 72 can be inserted smoothly into a tube cavity such as the esophagus of a living body.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasonic probe, comprising:

a long and narrow flexible sheath;

a cover member covering a hollow portion provided on a distal end side of the sheath in a liquid-tight manner;

an ultrasonic transducer, which is placed within the hollow portion covered by the cover member, for transmitting and receiving ultrasound;

an acoustic medium, which is filled around the ultrasonic transducer, for conducting ultrasound; and an acoustic window portion, which faces against a transmitting and receiving surface for transmitting and receiving ultrasound of the ultrasonic transducer in the cover member and which is formed of a resin including a mixture of polyamide block and polyether ester block copolymers and polyurethane, for allowing ultrasound to pass through.

2. An ultrasonic probe according to claim 1, wherein the entire cover member is formed of the resin provided with the acoustic window.

3. An ultrasonic probe according to claim 1, wherein the sheath is formed of the resin provided with the acoustic window.

4. An ultrasonic probe according to claim 1, wherein the cover member is integrated into the distal end of the sheath.

5. An ultrasonic probe according to claim 1, wherein the sheath is formed of a second resin including the mixture different from that of the resin provided with the acoustic window portion in mixing rates; and wherein the resin provided with the acoustic window portion has an acoustic impedance closer to that of a living body than that of the second resin.

6. An ultrasonic probe according to claim 1, wherein the acoustic window portion includes a plurality of layers containing polyamide block and polyether ester block copolymers and polyurethane in different mixing rates.

7. An ultrasonic probe according to claim 1, wherein the ultrasonic transducer is mechanically and rotationally driven.

8. An ultrasonic probe according to claim 1, wherein the ultrasonic transducer includes an acoustic lens on the transmitting and receiving surface side.

9. An ultrasonic probe according to claim 1, wherein the ultrasonic transducer is provided at the distal end side of a flexible shaft provided within the sheath.

10. An ultrasonic probe according to claim 1, wherein the sheath and a cover member constitute an inserting portion, which can be inserted through a tube cavity of a living body.

11. An ultrasonic probe according to claim 1, wherein the sheath and cover member constitute an inserting portion, which can be inserted through an endoscopic surgical instrument.

12. An ultrasonic probe according to claim 1, further comprising an illuminating optical system for optical illumination and an observation apparatus for optically observing a part illuminated by the illuminating optical system on the distal end side of the sheath.

13. An ultrasonic probe according to claim 12, wherein the observation apparatus has a solid-state image sensing device.

14. An ultrasonic probe according to claim 1, further comprising a motor on a base end side of the sheath for rotationally driving the ultrasonic transducer.

15. An ultrasonic probe according to claim 1, wherein the cover member is provided at the distal end of the sheath through a hard member.

16. An ultrasonic probe according to claim 15, wherein the hard member includes an illumination optical system for optically illumination and an observation apparatus for optically observing a part illuminated by the illumination optical system.

17. An ultrasonic probe according to claim 15, wherein the hard member includes a bearing portion for rotatably supporting a shaft having the ultrasonic transducer mounted in a liquid-tight manner.

18. An ultrasonic probe, comprising:
  an inserting portion including a long, narrow and flexible sheath;
  a sheath distal end portion provided on a distal end side of the sheath in a watertight manner;
  an ultrasonic transducer, which is placed within a hollow portion formed in the sheath distal end portion, for transmitting and receiving ultrasound; and
  an acoustic medium, which is filled in the hollow portion around the ultrasonic transducer, for conducting ultrasound,
  wherein the sheath and the sheath distal end portion are formed of a resin including a mixture of polyamide block and polyether ester block copolymers and polyurethane.

19. An ultrasonic probe according to claim 18, wherein the sheath and the sheath distal end are formed of first and second resins including the mixtures of polyamide block and polyether ester block copolymers and polyurethane in different mixing rates.

20. An ultrasonic diagnostic system, comprising:
  an ultrasonic probe having:
  an inserting portion including a long, narrow and flexible sheath; and
  an ultrasonic transducer accommodating cover portion provided at the distal end portion of the sheath for accommodating an ultrasonic transducer for transmitting and receiving ultrasound;
  an ultrasonic diagnostic equipment connected to the ultrasonic probe for performing signal processing for the ultrasonic transducer; and
  an acoustic window including a part, which faces against at least a transmitting and receiving surface for transmitting and receiving ultrasound by using the ultrasonic transducer in the ultrasonic transducer accommodating cover portion and which is formed of a resin including a mixture of polyamide block and polyether ester block copolymers and polyurethane.

* * * * *